United States Patent
Li et al.

(10) Patent No.: US 7,939,734 B1
(45) Date of Patent: May 10, 2011

(54) BIOCHEMICAL SENSORS USING CARBON NANOTUBE ARRAYS

(75) Inventors: Jun Li, Sunnyvale, CA (US); Meyya Meyyappan, San Jose, CA (US); Alan M. Cassell, Campbell, CA (US)

(73) Assignee: The United States of America as represented by the Administrator of the National Aeronautics and Space Administration (NASA), Washington, DC (US)

( * ) Notice: Subject to any disclaimer, the term of this patent is extended or adjusted under 35 U.S.C. 154(b) by 0 days.

(21) Appl. No.: 10/873,996

(22) Filed: Jun. 14, 2004

(51) Int. Cl.
*G01F 1/64* (2006.01)
*G01N 27/26* (2006.01)
*G01N 33/543* (2006.01)
*G01N 33/553* (2006.01)
*G01N 33/53* (2006.01)
*G01R 31/26* (2006.01)
*C12Q 1/00* (2006.01)
*C12M 1/00* (2006.01)
*C12M 1/34* (2006.01)

(52) U.S. Cl. ... 977/746; 205/775; 204/400; 204/403.01; 435/4; 435/287.1; 436/518; 436/525; 436/806; 438/14; 438/17; 977/702; 977/742; 977/745; 977/789; 977/904; 977/932; 977/953

(58) Field of Classification Search ............... 205/775; 204/400, 403.01; 435/4, 287.1; 436/518, 436/525, 806; 438/14, 17; 977/702, 742, 977/745, 746, 789, 904, 932, 953
See application file for complete search history.

(56) References Cited

U.S. PATENT DOCUMENTS

| | | | |
|---|---|---|---|
| 6,869,671 B1 * | 3/2005 | Crouse et al. | 428/304.4 |
| 6,905,655 B2 * | 6/2005 | Gabriel et al. | 422/82.01 |
| 2003/0218224 A1 * | 11/2003 | Schlaf et al. | 257/414 |
| 2004/0058153 A1 * | 3/2004 | Ren et al. | 428/408 |
| 2004/0106203 A1 * | 6/2004 | Stasiak et al. | 436/49 |
| 2004/0132070 A1 * | 7/2004 | Star et al. | 435/6 |
| 2004/0136866 A1 * | 7/2004 | Pontis et al. | 422/57 |
| 2004/0235016 A1 * | 11/2004 | Hamers et al. | 435/6 |
| 2005/0184294 A1 * | 8/2005 | Zhang | 257/77 |

OTHER PUBLICATIONS

J. Li, et al, The Highly Robust Electrical Interconnects and Ultrasensitive Biosensors Using Embedded Carbon Nanotube Arrays, 50th AVS Meeting, Nov. 5, 2003, Baltimore, Maryland.
J. Koehne, et al, "Ultrasensitive Label-free DNA Analysis Using an Electronic Chip Based on Carbo . . . ", Institute of Physics, Oct. 7, 2003, 1239-1245, 14, IOP Publishing Ltd, UK.
J. Koehne, et al, "The Fabrication and Electrochemical Characterization of Carbon Nanotube Nanoelectrode Arrays", Matr. Chem., Feb. 21, 2004, 676-684, 14.

(Continued)

*Primary Examiner* — N. C. Yang
(74) *Attorney, Agent, or Firm* — John F. Schipper; Robert M. Padilla (57) ABSTRACT

Method and system for detecting presence of biomolecules in a selected subset, or in each of several selected subsets, in a fluid. Each of an array of two or more carbon nanotubes ("CNTs") is connected at a first CNT end to one or more electronics devices, each of which senses a selected electrochemical signal that is generated when a target biomolecule in the selected subset becomes attached to a functionalized second end of the CNT, which is covalently bonded with a probe molecule. This approach indicates when target biomolecules in the selected subset are present and indicates presence or absence of target biomolecules in two or more selected subsets. Alternatively, presence of absence of an analyte can be detected.

21 Claims, 5 Drawing Sheets

OTHER PUBLICATIONS

J. Li, et al, "Carbon Nanotube Nanoelectrode Array for Ultrasensitive DNA Detection", Nano Letters, Mar. 22, 2003, 597-602, vol. 3, No. 5, American Chemical Society.

J. Li, Ultrasensitive Label-free Electronic Chips for DNA Analysis Using Carbon Nanotube Nanoel . . . , 36th Annual Oak Ridge Conference of the AACC, Apr. 29-30, 2004, San Jose, CA.

J. Li, Ultrasensitive Label-free Electronic Chips for DNA Analysis Using Carbon Nanotube Na . . . , Symposium on Mechanics & Chemistry of Biosystems, Feb. 9-10, 2004, UC Irvine, CA.

J. Li, Carbon Nanotube Nanoelectrode Array as an Electronic Chip for Ultrasensitive Label-free DNA Detection, Frontiers of Nanobio Research, Oct. 27, 2003, Taejong, Korea.

* cited by examiner

BIOCHEMICAL SENSORS USING CARBON NANOTUBE ARRAYS

ORIGIN OF THE INVENTION

This invention was made, in whole or in part, by one or more employees of the U.S. Government, which has the right to make, use and/or sell the invention without payment of royalties therefor.

FIELD OF THE INVENTION

This invention relates to sensing of presence and amount of specific chemical and biological molecules.

BACKGROUND OF THE INVENTION

The clinical laboratory is experiencing a revolution in reducing the cost and time required for molecular diagnostics. This development is increasingly important for implementing aspects of the Human Genome Project. A lack of procedures for quickly, accurately and inexpensively detecting presence of specific molecular signatures has become a bottleneck limiting use of relevant genetic information. Presently, molecular diagnostics is highly labor-intensive, with little automation or integration. Miniaturization technologies that integrate engineering capabilities and microelectromechanical systems (MEMS) with molecular biology expertise would allow molecular signature tests to be performed in microchips.

What is needed is an approach for quickly and accurately detecting presence of specific biological molecules ("biomolecules") that are of concern in molecular biology and related chemistry disciplines. Preferably, the procedure should allow detection of a specific molecule and/or of a class of related molecules, should be flexible, and should permit automation and integration of the procedure with other related biological and chemical procedures.

SUMMARY OF THE INVENTION

These needs are met by the invention, which provides an array of carbon nanotubes, each with a first end electrically connected to an electronics device, and with a second (exposed) end being functionalized with a selected molecule attached thereto that provides an electrochemical or other signal that is recognized by the electronics device.

A novel biosensor platform and relevant electrochemical detection methods are developed using a vertically aligned carbon nanotube array, with nanoelectrodes embedded in dielectric materials such as $SiO_2$, $Si_3N_4$ or suitable polymers. The dielectric encapsulation provides mechanical robustness and electrical isolation of the individual nanoelectrodes.

A first end of each carbon nanotube is attached to one or more metal electrodes or contacts, and a portion of a second end of a carbon nanotube is exposed at the surface of the dielectric layer and is covalently functionalized with one or more biomolecule probes, such as oligonucleotides, peptides, proteins, enzymes, etc. through the formation of amide bonds. One, two or more different sub-arrays of functionalized CNT ends are provided, where each sub-array consists of a type of biomolecule that can specifically bind with a biomolecule marker in the sample solution that is associated with a particular genetic sequence of disease or condition, or is linked with enzymes that can catalyze a specific reaction.

The binding of the target molecules (biomolecule markers), through specific interaction with the probe molecules functionalized at the CNT ends, is to be detected by electrochemical methods. This technique can be implemented through disposable cartridges in hand-held devices or work stations for quick identification of biomarkers. This approach can be also used as a detector to enhance the performance of other systems such as separation instruments including chromatography or microfluidics devices.

Electrochemical methods are attractive for development of biosensors because such a sensor can directly interface the biomolecules in physiological environments with microelectronics circuits. The sample handling, signal processing, and device fabrication can be dramatically simplified by use of mature microfabrication techniques. However, the sensitivity is normally lower than other techniques such as laser fluorescence. By introducing embedded carbon nanotube nanoelectrode array on top of the multiplex microelectrodes, it provides the following advantages: (1) much smaller number of target molecules required (since the active surface area is only a very small fraction of the microelectrode surface), (2) fast detection due to much higher temporal resolution, (and make it possible to use advanced pulsed electronic techniques such as differential pulse voltammetry, AC voltammetry, square-wave voltammetry, electrochemical impedance spectroscopy (EIS), etc. in addition to conventional cyclic voltammetry, potentiometry, amperometry, etc.), and (3) much higher sensitivity as a result from (1) and (2). In addition, catalytic mediators can be added to the buffer solutions so that the electrochemical signal can be amplified further.

Previous studies may have used similar catalytic mediators or enzymatic mechanisms, but are limited by the poor signal-to-noise ratio associated with the large solid electrode diameter (typically>30 microns), poor stability (due to weak binding of organic films on electrode surface) and/or small potential windows for the electrode materials. By comparison, carbon nanotubes are biocompatible, have a wide potential window, and can be selectively functionalized through strong covalent binding. Many functional groups in biomolecules, such as guanine bases, can be directly measured with carbon nanotube electrodes. The nanoscale electrode size can dramatically improve the performance in terms of sensitivity (i.e., signal-to-background ratio and signal-to-noise ratio), temporal resolution, and stability.

The innovation includes the following technical features.

(1) Using vertical aligned carbon nanotube nanoelectrode arrays as the sensing element: The CNTs efficiently interconnect biomolecules with electronic circuits, and the sidewalls and circuits are encapsulated by insulating dielectrics to minimize the background noise. A method is developed to control the density of active carbon nanotube nanoelectrodes by lithography or controlling the endpoints of chemical mechanical polishing, plasma etching and/or chemical etching. A separation over at least six times of the radius of each nanoelectrode is desired to avoid the overlapping of the diffusion layers around neighboring electrodes.

(2) Functionalization and/or passivation (optional): An electrochemical etching step in NaOH solution is developed to prepare a well-defined —COOH rich carbon nanotube end for reliable functionalization through amide bonds, which is highly selective to carbon materials. The rest of the surface is passivated with poly ethylene glycol molecules through silane chemistry. This ensures that active probe molecules only attach to the desired active CNT sites. Alternatively, portions of the matrix surface (insulating material) can be functionalized instead of functionalization of the CNT sites.

(3) Electrochemical detection: Pulsed electrochemical techniques such as differential pulse voltametry, AC voltametry, square-wave voltametry, electrochemical impedance spectroscopy, fast scan cyclic voltammetry, etc. can be employed in addition to conventional cyclic voltammetry, potentiometry, amperometry for appropriate sensor application for improving sensitivity.

(4) A separate electrode or subsequent measurements on the same electrode (for irreversible reactions) can be used as control to ensure the correct measurements.

A potential benefit of biosensors based on carbon nanotube nanoelectrode arrays is the dramatically improved sensitivity and reliability. Such features can enable the realization of many other advantages of electronic techniques such as miniaturization, multiplexing, low cost, simple operation, and quick detection, which are highly demanded for quick biomolecular analysis. It may find applications in space program, homeland protection, environmental monitoring, point-of-care, early disease diagnosis, and biomedical treatments. The detection technique may be also used in other analytical instruments such as chromatography and microfluidics, with or without functionalization of the exposed CNT ends with biomolecules.

DESCRIPTION OF BEST MODES OF THE INVENTION

A carbon nanotube (CNT) is a regular geometric structure of covalently connected C atoms, such as a cylindrical structure with a substantially constant or variable diameter that may range from 1 nanometer (nm) to tens or hundreds of nm, resembling a hollow tube. A CNT is normally grown from, and oriented approximately perpendicular to, a substrate with a specially prepared surface and can reach a vertical height of 100 nm to 20 μm, or higher, before the structure begins to "droop" and depart from a vertical orientation. The structure may have a single layer or a multiple layer of C atoms. An exposed end of a C atom chain may be functionalized to bond to a class of other molecules.

Figure 1A:
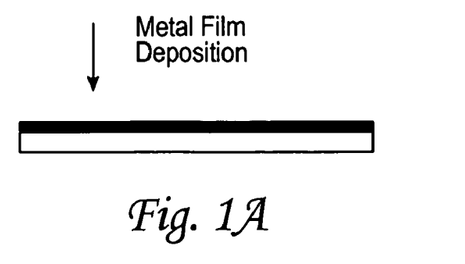
FIGS. 1A-1G schematically illustrate fabrication of an array of CNTs on a substrate.
Figure 1B:
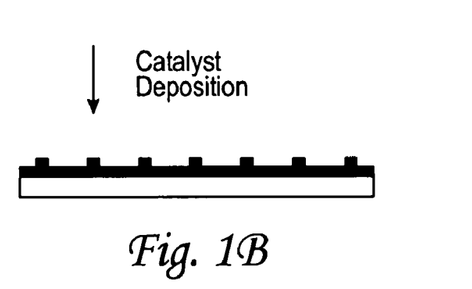
Figure 1C:
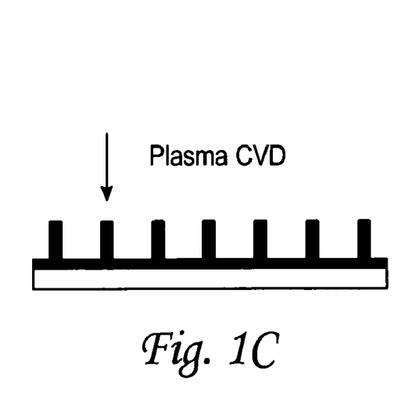
Figure 1D:
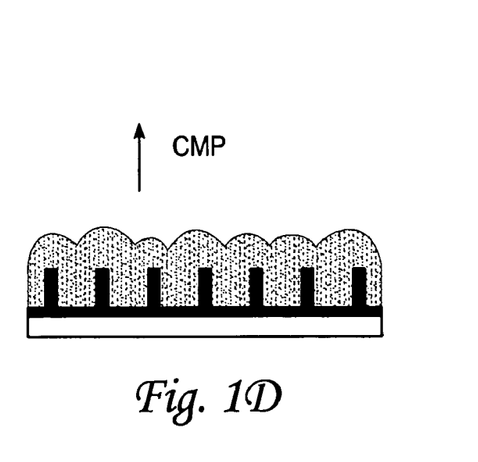
Figure 1E:
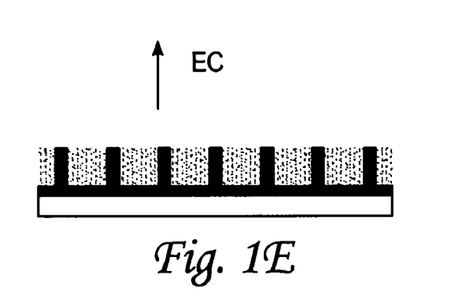
Figure 1F:
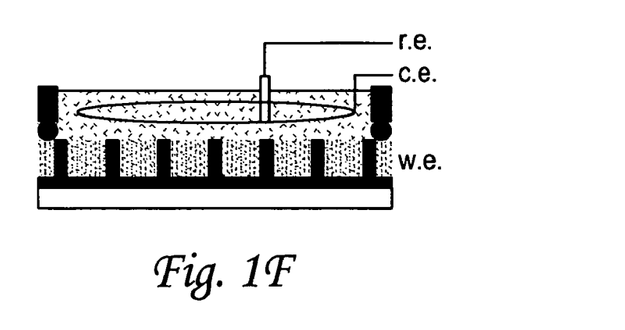
Figure 1G:
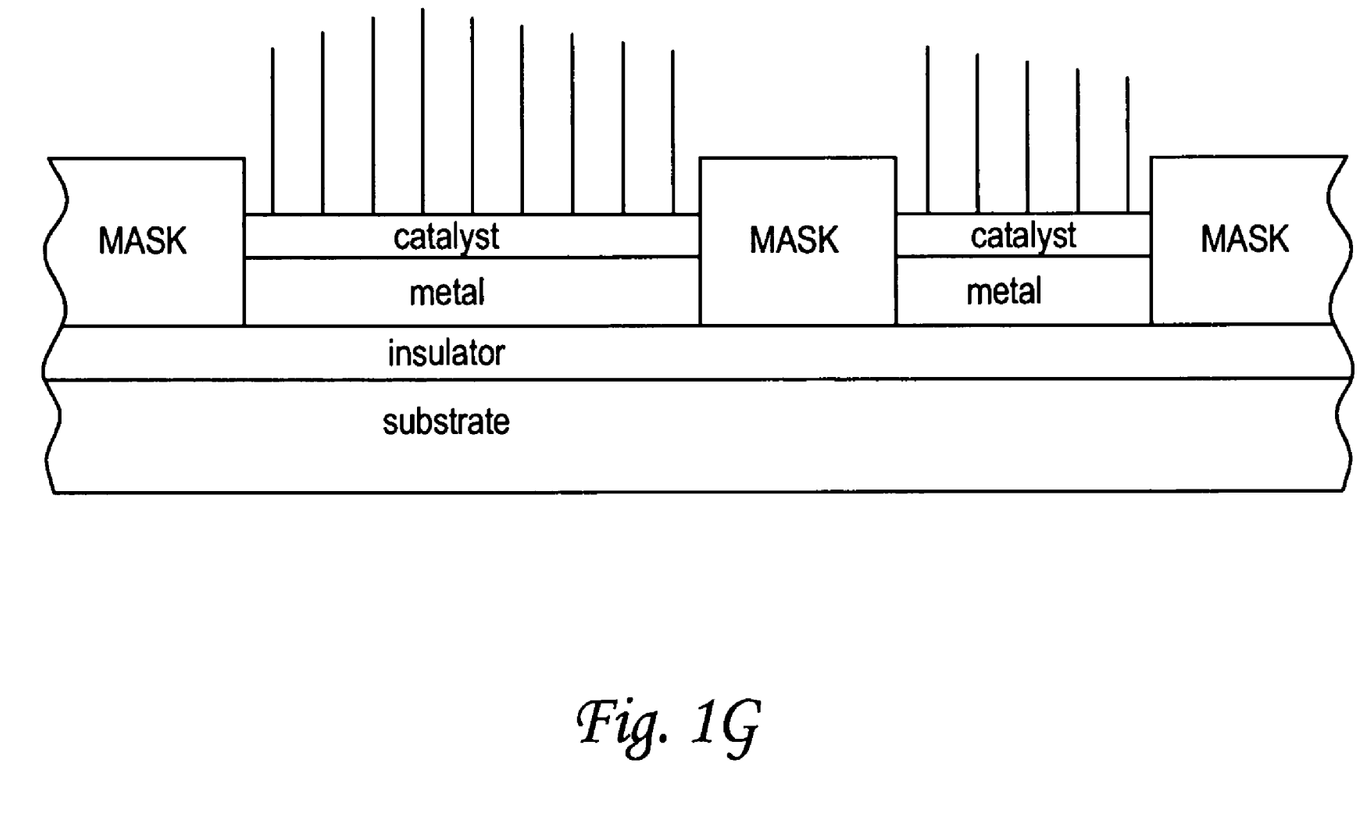

A CNT can be fabricated using a procedure such as the following, illustrated in FIGS. 1A-1F. A metal film, such as Cr, Pt, Pd, Ti, and/or Mo, typically about 200 μm thick, is deposited onto a Si wafer that is covered with about 500 nm of $SiO_2$ or $Si_3N_4$ (FIG. 1A). The metal film serves as an electrical contact that can be patterned as desired. A Ni catalyst film of thickness 10-30 nm is deposited at one or more desired (pattern) locations on the metal contact (FIG. 1B). The Ni film at each location can be patterned as an array of dots, each having a diameter no greater than 100 nm, or as one or more spots having a diameter from less than 1 μm to hundreds of μm, or as a continuous film over the entire pattern. A vertically aligned multiwall CNT array is grown on the Ni catalyst, using plasma enhanced chemical vapor deposition (PECVD, FIG. 1C). A film of $SiO_2$ with thickness 2-5 μm is deposited using thermal CVD of tetraethylorthosilicate (TEOS) at a temperature T=650-750° C. and TEOS vapor pressure 400 mTorr, providing a conformal film that encapsulates each CNT and the substrate surface (FIG. 1D). The extra $SiO_2$ at the top surface of the substrate is removed by chemical/mechanical polishing (CMP), mechanical polishing, chemical etching, plasma etching or a similar process, so that one end of some of the CNTs is exposed (FIG. 1E). Electrochemical measurements are performed on the product, for example, using a three-electrode configuration (FIG. 1F). FIG. 1G (not drawn to scale) schematically illustrates a result of the process steps shown in FIG. 1A-1B for patterned multiple metal contacts.

Figure 2:
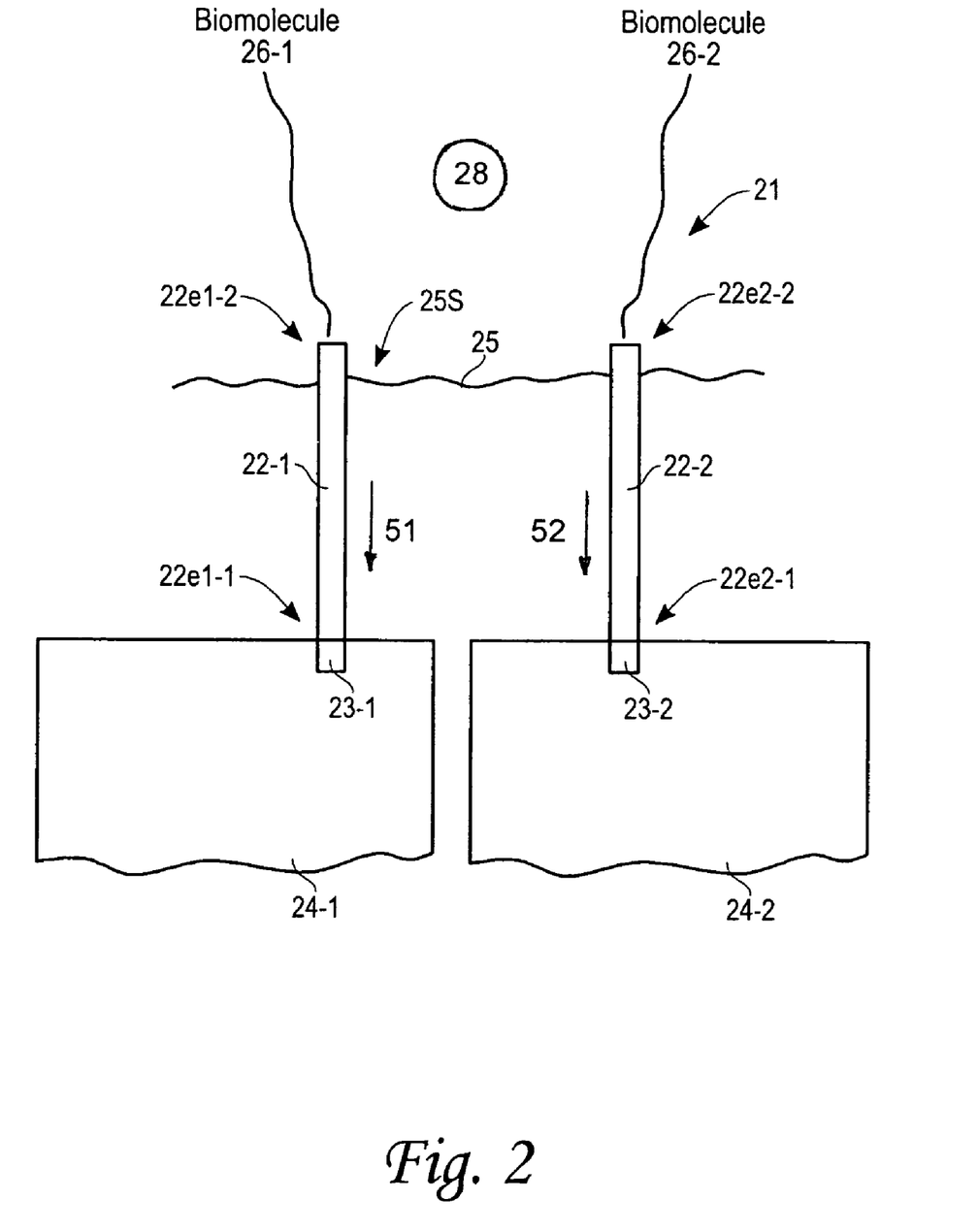
FIG. 2 schematically illustrates apparatus for practicing the invention.

FIG. 2 schematically illustrates a system 21 incorporating the invention. A first sub-array 22-1 and a second sub-array 22-2 of vertically oriented CNTs, having respective first sub-array electrodes 23-1 and second sub-array electrodes 23-2, are electrically connected to a first signal processing device 24-1 and to a second signal processing device 24-2, respectively, at first ends 22e1-1 and 22e2-1 of the CNTs. The first sub-array 22-1 of CNTs and the second sub-array 22-2 of CNTs may be intermingled with each other or may be spaced apart from and isolated from each other. Interstitial space between adjacent CNTs, whether from the same sub-array or from a different sub-array, is partly or wholly filled with an insulating material 25, such as $SiO_x$ or $Si_yN_z$ or suitable polymers, to reduce or eliminate cross-talk or other electromagnetic interference between two adjacent (or non-adjacent) CNTs. The insulating material 25 is processed, by mechanical polishing, by chemical mechanical polishing (CMP), by plasma etching, by wet chemical etching, or by another suitable technique, so that a second end 22e1-2 of the first sub-array 22-1 of CNTs and a second end 22e2-2 of the second sub-array 22-2 of CNTs is either fully exposed or is flush with an exposed surface 25s of the insulating material.

A second end 22e1-2 of each CNT in the first sub-array 22-1 is functionalized so that a first subset of biomolecules 26-1 from a first class of biomolecules (probe molecules) can attach itself to the second end 22e1-2 of the first sub-array CNT. A second end 22e2-2 of each CNT in the second sub-array 22-2 is functionalized so that a second subset of biomolecules 26-2 from the first class of biomolecules can attach itself to the second end 22e2-2 of the second sub-array CNT. Preferably, the first and second subsets of the first class of biomolecules (probe molecules) are confined exclusive to the respective sub-arrays 22-1 and 22-2 so that no first subset biomolecule can attach itself to the second end 22e2-2 of a member of the second CNT sub-array 22-2, and no second subset biomolecule can attach itself to the second end 22e1-2 of a member of the first CNT sub-array 22-1.

A fluid 28, which may or may not include biomolecules from the second class of biomolecules (target molecules), is positioned contiguous to, or flows through, the functionalized second ends, 22e1-2 and 22e2-2, which initially have biomolecules from the first class attached thereto. Each biomolecule from a first subset of the second class specifically bonds only with a particular subset biomolecule from the first class. If, for example, the fluid 28 contains biomolecules from the first subset of the second class, some of these biomolecules will attach themselves to the first subset of the first class of biomolecules of functionalized second ends 22e1-2 of the first sub-array CNTs, and this will produce an electromagnetic signal S1 that is received and sensed by the first signal processing device 24-1. Similarly, if the fluid 28 contains biomolecules from the second subset from the second class, some of these biomolecules will attach themselves to the second subset of the first class of biomolecules of the functionalized second ends 22e2-2 of the second sub-array CNTs, and this will produce an electromagnetic signal S2 that is received and sensed by the second signal processing device 24-2 (which, optionally, may coincide with the first signal processing device 24-1). The signals S1 and S2 may be the same or may be different.

In this version, it is assumed that only the presence of a sufficient density or absolute number of the first subset of target biomolecule will produce a signal S1, and only the presence of a sufficient density or absolute number of the second subset of target biomolecule will produce a signal S2, whether S1 is the same as S2 or different from S2. If the signals S1 and S2 differ substantially from each other, the first signal processing device 24-1 and the second signal processing device 24-2 can be the same device, and the distinction between the signals S1 and S2 is made within this device.

Figure 3A:
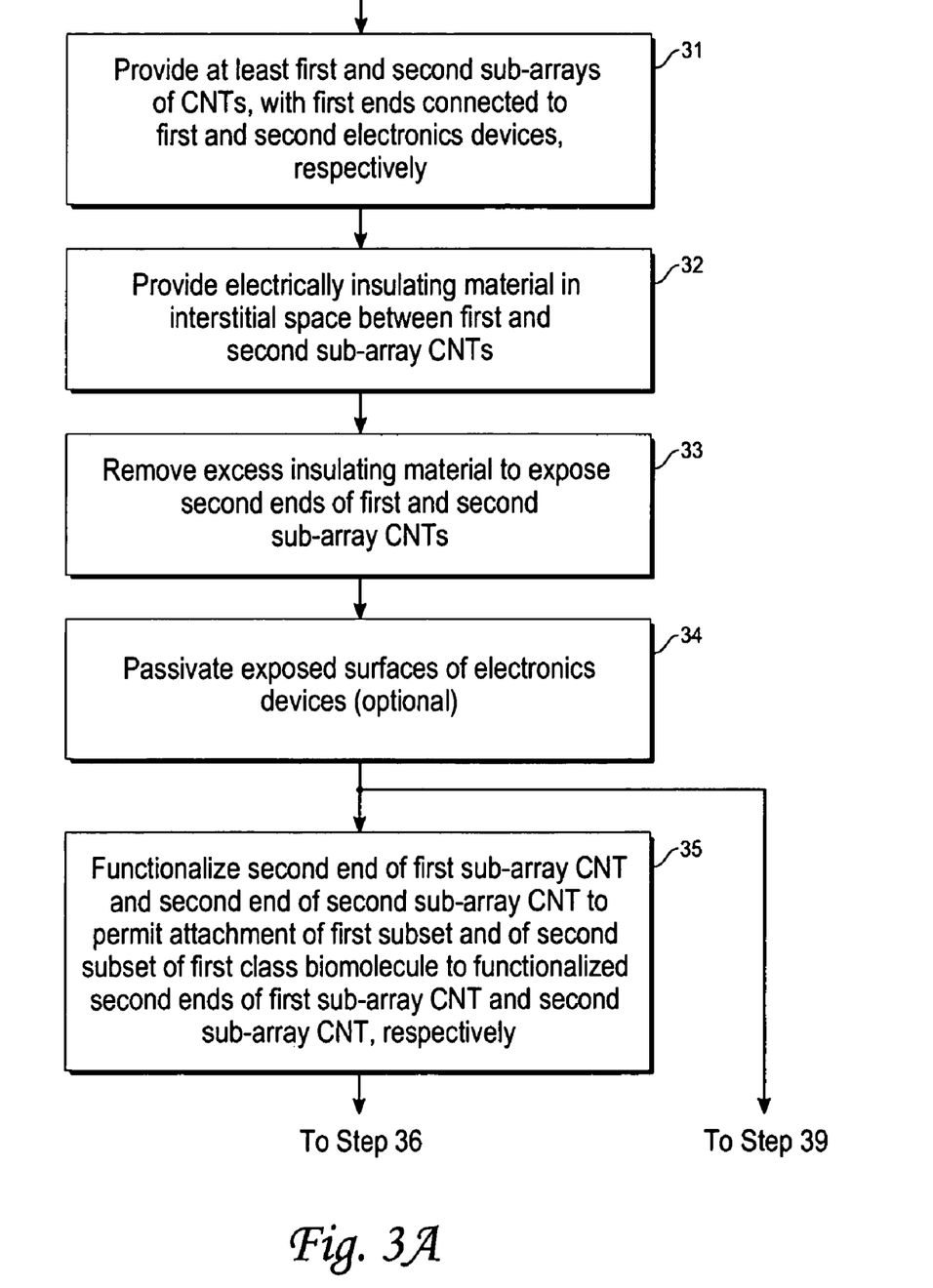
FIG. 3 is a flow chart of a procedure for practicing the invention.
Figure 3B:
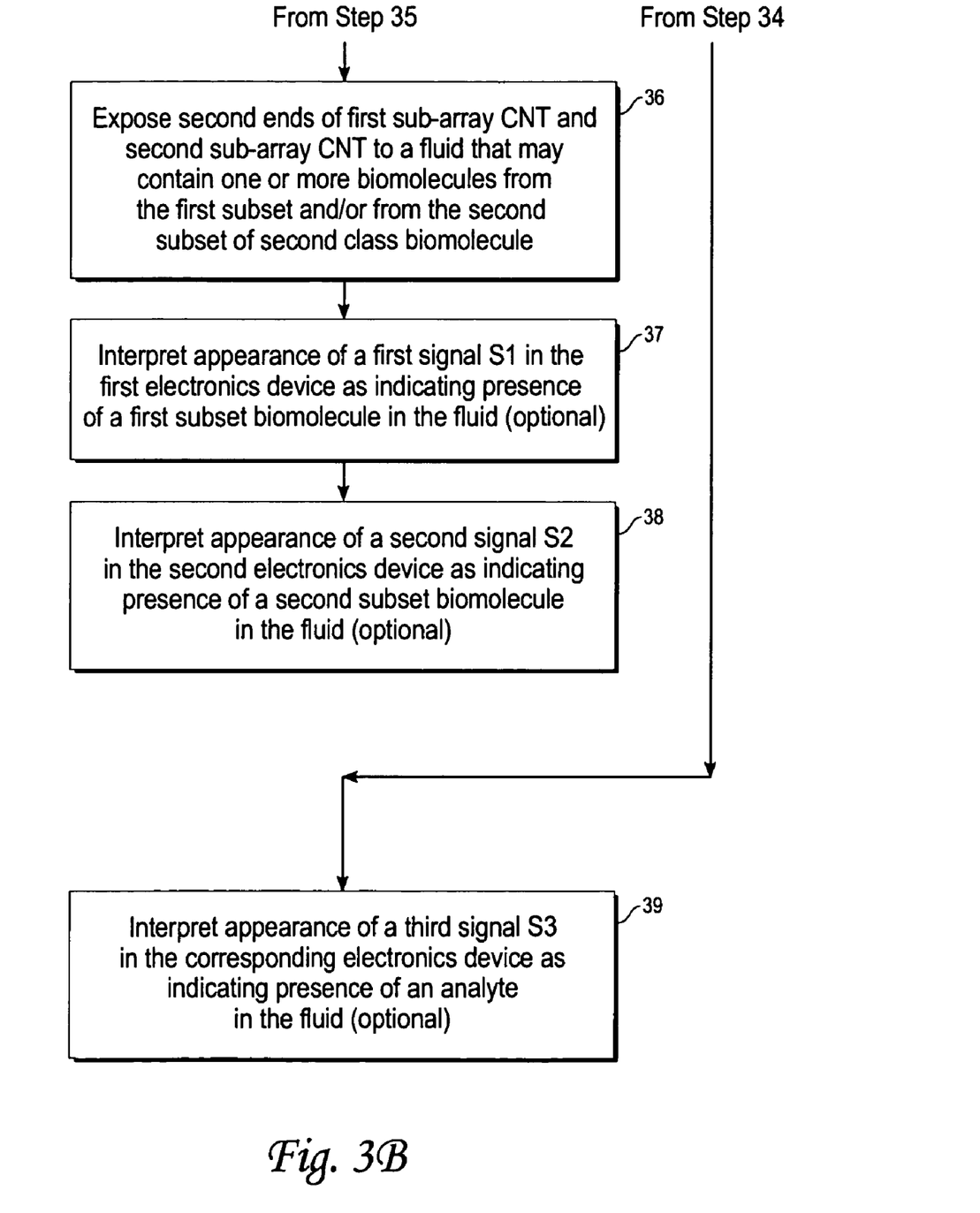

In some applications, functionalization of the first class of biomolecules (probe molecules) may be deleted. In this approach, a third class of molecules, referred to as analytes (not necessarily having specific biorecognition properties), may be introduced into the fluid 28. The third class may be biomolecules or other molecules. Where an analyte is used, functionalization of exposed second ends of CNTs need not be performed. An analyte may allow or facilitate production of a third signal S3 in a corresponding electronics device. In step 38 (optional), appearance of a fourth electromagnetic signal S4 in the second electronics device is interpreted as indicating that the second subset of the third class of molecule is present in the fluid.

FIG. 3 is a flow chart illustrating a procedure for constructing a system for practicing the invention. In step 31, an array of at least two CNTs is provided. A first end of each CNT in a first sub-array is electrically connected to a first electronics device that provides a first electromagnetic signal S1 when a first biomolecule becomes connected to a CNT in the first sub-array. A first end of each CNT in a second sub-array is electrically connected to a second electronics device (which may be the same as or different from the first electronics device) that provides a second electromagnetic signal S2 when a second biomolecule becomes connected to a CNT in the second sub-array.

In step 32, an electrically insulating material is provided in an interstitial space between a first CNT in the first sub-array and an adjacent second CNT in the second sub-array, and also between the underlying metal lines, so that a second end of the first sub-array CNT and a second end of the second sub-array CNT are exposed. Preferably, the insulating material separates each CNT from all adjacent CNTs, whether the adjacent CNTs are from the same sub-array or from a different sub-array. The insulating material may be chosen from among $SiO_x$, $Si_yN_z$, and suitable polymers, such as epoxy, wax and parylene.

In step 33, excess insulating material is removed to expose a second end of one or more of a CNT in the first sub-array and of one or more of a second end of a CNT in the second sub-array, using CMP, mechanical polishing, plasma etching, wet chemical etching or another suitable material removal procedure.

In step 34 (optional), the exposed surfaces of the device are passivated, using non-specific resisting molecules, such as polyethylene glycol (PEG), to reduce non-specific adsorption of biomolecules. From step 34, the system moves to step 35 or, alternatively, to step 39.

In step 35 (optional), the second end of the first sub-array CNT is functionalized by a first selected functionalization process, and the second end of the second sub-array CNT is functionalized by a second selected functionalization process. Functionalization of the second end of the first sub-array CNT allows a first subset from a first biomolecule class (probe molecule) to attach itself to this second end of the first sub-array CNT, if the subset of probe first biomolecule is present in a fluid medium to which the second end of the first sub-array CNT is exposed. Functionalization of the second end of the second sub-array CNT allows a biomolecule from a second subset of the first biomolecule class to attach itself to this second end of the second sub-array CNT, if the second subset biomolecule is present in a fluid medium to which the second end of the second sub-array CNT is exposed. Functionalization is preferably performed sequentially by activating a sub-array of CNTs with electrochemical etching, then introducing a specific subset of biomolecules. This process can also be performed by applying a specific subset of the first class of molecules at specific sub-array sites.

In step 36, the (functionalized) second ends of the first sub-array CNT and the second sub-array CNT and the insulating material are exposed to a fluid that may contain the a biomolecule from the second class. If and only if the fluid contains the first subset of the second class biomolecule (target biomolecule) with a sufficient density or amount, a signal S1 will be sensed by the first electronics device. If and only if the fluid contains the second subset of the second class biomolecule (target biomolecule) with a sufficient density or amount, a signal S2 will be sensed by the second electronics device. If and only if the fluid contains a specific analyte, a third signal S3 is sensed by the corresponding electronics device.

Each subset of the first class biomolecule may be chosen from a class of oligonucleotides, peptides, proteins and/or enzymes. The second class biomolecule may be an oligonucleotide, a segment of DNA, RNA, protein, bacterium or non-biological substance that undergoes strong bonding with the first class biomolecule.

Preferably, the first subset of the first class of biomolecules and the second subset of the first class of biomolecules are mutually exclusive. In another version, the first and second subsets of the first class of biomolecules coincide so that the system indicates the presence (or probable absence) of only one subset of the second class of biomolecules.

In step 37 (optional), appearance of the first electromagnetic signal in the first electronics device is interpreted as indicating that the first subset of the second class of biomolecule is present in the fluid.

In step 38 (optional), appearance of the second electromagnetic signal in the second electronics device is interpreted as indicating that the second subset of the second class of biomolecule is present in the fluid. If no analytes in the solution are of interest, the procedure ends here.

In step 39 (optional), reachable through step 34, appearance of a third electromagnetic signal S3 in the corresponding electronics device is interpreted as indicating that a analyte (corresponding to S3) is present in the fluid. The analyte may be a biomolecule (such as a nucleic acid, a protein, a nucleotide, a peptide, a neurotransmitter, a hormone, an orgainic molecules (e.g., a pesticide, an amine, a phenol, etc.), or an inorganic molecules (e.g., heavy metal ion, halide, metal complex, $H_2O_2$, $NO_x$, etc.). The signal S3 may, for example, relate electrical current and voltage difference, measured or applied, between a CNT second end and a reference electrode, which is characteristic for a specific analyte.

What is claimed is:

1. A method for sensing presence of a target biomolecule in a liquid solution, the method comprising:
    providing an array of at least first and second carbon nanotubes (CNTs), where a first end of each of the at least first and second CNTs is electrically connected by at least one signal carrying line to, and is oriented substantially perpendicular to a surface of, an electronics device that transduces or otherwise provides an identifiable change in an electrochemical signal when a target biomolecule becomes attached to or interacts with at least one CNT in the array, where the electrochemical signal is at least one of a differential pulse voltammetry signal, an AC voltammetry signal, a square wave voltammetry signal, and an electrochemical impedance spectroscopy signal, a fast scan cyclic voltammetry signal, a conventional cyclic voltammetry signal, a conventional potentiometry signal, and a conventional amperometry signal;

providing an electrically insulating material that substantially fills an interstitial space between, and substantially covers surfaces of, the first and second CNTs and the at least one signal carrying line, and removing a sufficient amount of the insulating material to expose a second end of the first CNT and a second end of the second CNT, by at least one of mechanical polishing, chemical mechanical polishing, plasma etching and chemical etching, to prevent attachment of a probe biomolecule to a side surface of the first and second CNTs;

providing a surface passivation layer on exposed surfaces of the interstitial insulating material, to suppress attachment of a biomolecule in an adjacent liquid solution to the surface of the interstitial insulating material;

electrochemically etching the surface passivation layer at selected locations to expose the second end of the first and second CNTs;

functionalizing the second end of the first and second CNTs with a probe biomolecule that can interact with or become attached to the second end of the first and second CNTs, where the probe biomolecule is at least one of an oligonucleotide, a peptide, a ligand, a protein and an enzyme;

immersing the second end of the first and second CNTs in the liquid solution that may contain at least one target biomolecule;

when the target biomolecule is present in the solution, allowing the target biomolecule to interact with or become attached to the probe biomolecules at the functionalized second end of the first and second CNTs and to generate a change in an electrochemical signal of at least one of the functionalized first and second CNTs;

interpreting lack of receipt of the change in the electrochemical signal as indicating that at least one of the following conditions is present: (i) no target biomolecule is present in the solution and (ii) the target biomolecule is present in the solution in an amount that is less than a threshold amount; and interpreting receipt of the change in the electrochemical signal as indicating that at least one target biomolecule is present in the solution in an amount at least equal to the threshold amount.

2. The method of claim 1, further comprising choosing said insulating material from the group of insulating materials consisting of $SiO_x$, $Si_yN_z$, an epoxy, a wax and a parylene, where x, y and z are positive numbers.

3. A method for sensing presence of selected first and second target biomolecules, the method comprising:

providing at least a first carbon nanotube (CNT) in a first sub-array and at least a second CNT in a second sub-array, where a first end of each first sub-array CNT is electrically connected by a first signal carrying line to, and is oriented substantially perpendicular to, a surface of, a first electronics device that transduces or otherwise provides a change in a first electrochemical signal of the first sub-array CNT when a first target biomolecule interacts with or becomes attached to a first probe biomolecule located on a second end of the first sub-array CNT, and where a first end of each CNT in the second sub-array is electrically connected by a second signal carrying line to, and is oriented substantially perpendicular to a surface of, a second electronics device that transduces or otherwise provides a change in a second electrochemical signal of the second sub-array CNT when a second target biomolecule interacts with or becomes attached to a second probe biomolecule located on a second end of the second sub-array CNT, where each of the first and second electrochemical signals is at least one of a differential pulse voltammetry signal, an AC voltammetry signal, a square wave voltammetry signal, and an electrochemical impedance signal spectroscopy signal, a fast scan cyclic voltammetry signal, a conventional cyclic voltammetry signal, a conventional potentiometry signal, and a conventional amperometry signal;

providing an electrically insulating material that substantially fills an interstitial space between the first sub-array CNT, and the second sub-array CNT, and substantially covers the first signal carrying line and the second signal carrying line, and removing a sufficient amount of the interstitial insulating material to expose the second end of the first sub-array CNT and the second end of the second sub-array CNT, by at least one of mechanical polishing, chemical mechanical polishing, plasma etching and chemical etching, to insulate the first and second sub-array CNTs and to prevent attachment of a probe biomolecule to a side surface of the first sub-array CNT and to a side surface of the second sub-array CNT;

providing a surface passivation layer on exposed surfaces of the interstitial insulating material, to suppress attachment of a biomolecule in an adjacent liquid solution to the surface of the interstitial insulating material;

electrochemically etching the surface passivation layer at a first selected location to expose the second end of the first sub-array CNT;

functionalizing the second end of the first sub-array CNT with a first probe biomolecule so that the first target biomolecule can interact with or become attached to the first probe biomolecule at a second end of the first sub-array CNT and so that a probe biomolecule that is introduced subsequent to functionalization with the first probe biomolecule has no access to the second end of the first sub-array CNT;

electrochemically etching the surface passivation layer at a second selected location to expose the second end of the second sub-array CNT;

functionalizing the second end of the second sub-array CNT with a second probe biomolecule so that the second target biomolecule can interact with or become attached to the second probe biomolecule at a second end of the second sub-array CNT;

immersing the second ends of the first sub-array CNT and the second sub-array CNT in the liquid solution that may contain the first target biomolecule and that may contain the second target biomolecule;

when at least one of the first target biomolecule and the second target biomolecule is present in the solution, allowing at least one of the first target biomolecule and the second target biomolecule to interact with or become attached to at least one of the respective first probe molecule and second probe molecule on the functionalized second end of at least one of the first sub-array CNT and the second sub-array CNT;

interpreting lack of receipt of change in the first electrochemical signal of the first sub-array functionalized CNT at the first electronics device as indicating at least one of: (i) the first target biomolecule is not present in the solution and (ii) the first target biomolecule is present in the solution in an amount that is less than a first threshold amount;

interpreting receipt of change in the first electrochemical signal of the first sub-array functionalized CNT at the first electronics device as indicating that the first target biomolecule is present in the solution in an amount at least equal to the first threshold amount;

interpreting lack of receipt of change in the second electrochemical signal of the second sub-array functionalized CNT at the second electronics device as indicating at least one of: (i) the second target biomolecule is not present in the solution and (ii) the second target biomolecule is present in the solution in an amount that is less than a second threshold amount; and interpreting receipt of change in the second electrochemical signal of the second sub-array functionalized CNT at the second electronics device as indicating that the second target biomolecule is present in the solution in an amount at least equal to the second threshold amount.

4. The method of claim 3, further comprising choosing said insulating material from the group of insulating materials consisting of $SiO_x$, $Si_yN_z$, an epoxy, a wax and a parylene, where x, y and z are positive numbers.

5. The method of claim 3, further comprising choosing said first probe biomolecule to be at least one of an oligonucleotide, a peptide, a ligand, a protein and an enzyme.

6. The method of claim 3, further comprising choosing said second probe biomolecule to be at least one of an oligonucleotide, a peptide, a ligand, a protein and an enzyme.

7. The method of claim 1, further comprising choosing said surface passivation layer to comprise polyethylene glycol.

8. The method of claim 3, further comprising choosing said first target biomolecule and said second target biomolecule to be distinguishable from each other.

9. The method of claim 3, further comprising choosing a signal associated with said first electrochemical signal of the first sub-array functionalized CNT and a signal associated with said second electrochemical signal of the second sub-array functionalized CNT to be distinguishable from each other.

10. The method of claim 1, further comprising providing said probe molecule as an $NH_2$-containing molecule that can form at least one amide bond with a carboxylic acid group at an exposed second end of at least one of said first CNT and said second CNT.

11. The method of claim 1, further comprising separating said first and second CNTs by a separation distance of at least six times a maximum of a radius of said first CNT and a radius of said second CNT.

12. The method of claim 3, further comprising choosing said surface modification layer to comprise polyethylene glycol.

13. The method of claim 3, further comprising providing at least one of said first probe biomolecule and said second probe biomolecule as an $NH_2$-containing molecule that can form at least one amide bond with a carboxylic acid group on an exposed second end of at least one of said first sub-array CNT and said second sub-array CNT.

14. The method of claim 3, further comprising separating said first CNT in said first sub-array by a separation distance of at least six times a maximum of a radius of said first CNT from a second CNT in said first sub-array.

15. The method of claim 1, further comprising:
measuring a first change of said electrochemical signal between a first measurement time and a second measurement time;
measuring a second change of said electrochemical signal between two measurement times that are subsequent to the first measurement time;
comparing the first change and the second change of said electrochemical signal with each other; and
when the first change and the second change differ from each other by at least a threshold value, interpreting this as indicating that said target biomolecule is present in said solution.

16. The method of claim 15, further comprising providing at least one of said first change of said electrochemical signal and said second change of said electrochemical signal as an irreversible change.

17. The method of claim 3, further comprising providing at least a third sub-array CNT having a second end that is exposed by said electrochemical etching but is not functionalized and does not bind with said first target biomolecule and does not bind with said second target biomolecule, to provide a control signal to indicate if said functionalization by said first probe biomolecule at said second end of said first sub-array CNT distinguishes between said binding of said first target biomolecule and binding of a biomolecule that is not said first target biomolecule.

18. The method of claim 1, further comprising forming said surface passivation layer using silane chemistry.

19. The method of claim 3, further comprising forming said surface passivation layer using silane chemistry.

20. The method of claim 3, wherein said functionalization of said second end of said first sub-array CNT comprises:
providing at least one species of primary amine-terminated small molecule that forms an amide bond with an unreacted COOH group located on said second end of said first sub-array CNT, before at least one of said second end of said first sub-array is exposed to said second probe biomolecule.

21. The method of claim 3, wherein said functionalization of said second end of said first sub-array CNT comprises:
providing said first probe molecules in a close-packed format at said second end of said first sub-array CNT so that access of said second probe biomolecules to said second end of said first sub-array CNT is blocked.

* * * * *